United States Patent
Sen et al.

(10) Patent No.: US 10,238,629 B2
(45) Date of Patent: Mar. 26, 2019

(54) METHODS FOR REDUCING THE OCCURRENCE OF HOT FLASHES

(71) Applicant: Ohio State Innovation Foundation, Columbus, OH (US)

(72) Inventors: Chandan K. Sen, Upper Arlington, OH (US); Sashwati Roy, Upper Arlington, OH (US); Savita Khanna, Columbus, OH (US); Cameron Rink, Lewis Center, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 133 days.

(21) Appl. No.: 14/906,695

(22) PCT Filed: Jul. 22, 2014

(86) PCT No.: PCT/US2014/047633
§ 371 (c)(1),
(2) Date: Jan. 21, 2016

(87) PCT Pub. No.: WO2015/013285
PCT Pub. Date: Jan. 29, 2015

(65) Prior Publication Data
US 2016/0166535 A1    Jun. 16, 2016

Related U.S. Application Data

(60) Provisional application No. 61/857,087, filed on Jul. 22, 2013.

(51) Int. Cl.
| | | |
|---|---|---|
| A61K 31/355 | (2006.01) | |
| A61K 9/107 | (2006.01) | |
| A61K 9/48 | (2006.01) | |
| A61K 45/06 | (2006.01) | |

(52) U.S. Cl.
CPC ............ *A61K 31/355* (2013.01); *A61K 9/107* (2013.01); *A61K 9/4858* (2013.01); *A61K 9/4866* (2013.01); *A61K 9/4875* (2013.01); *A61K 45/06* (2013.01)

(58) Field of Classification Search
CPC .................................................. A61K 31/355
See application file for complete search history.

(56) References Cited

U.S. PATENT DOCUMENTS

| | | |
|---|---|---|
| 2002/0068100 A1 | 6/2002 | Kapoor et al. |
| 2004/0048919 A1 | 3/2004 | Dreon et al. |
| 2008/0146541 A1 | 6/2008 | Wu |
| 2009/0041870 A1 | 2/2009 | Tan et al. |
| 2009/0110674 A1 | 4/2009 | Loizou |
| 2011/0245182 A1 | 10/2011 | Perricone |
| 2011/0293743 A1 | 12/2011 | Perricone |
| 2012/0122969 A1 | 5/2012 | Miller |

FOREIGN PATENT DOCUMENTS

| | | |
|---|---|---|
| WO | 0002553 A1 | 1/2000 |
| WO | 2011161655 A1 | 12/2011 |

OTHER PUBLICATIONS

Stearns et al., Hot Flashes, 2002, The Lancet, vol. 360, pp. 1851-1861.*
Sen et al., Tocotrienols: Vitamin E Beyond Tocopherols, 2006, Life Sci., 78(18), pp. 2088-2098.*
Jones et al., Androgen deprivation therapy-associated vasomotor symptoms, 2012, Asian Journal of Andrology, 14, pp. 193-197 (Year: 2012).*
Examination Report issued in Australian Application No. 2014293314, dated Jul. 25, 2017.
Ziaei, S. et al., "The effect of vitamin E on hot flashes in menopausal women.", Gynecologic and Obstetric Investigation, 2007; 64(4), pp. 204-207; XP055344717, Retrieved from the Internet: URL:http://www.ncbi.nlm.nih.gov/pubmed/17664882 [retrieved on Feb. 10, 2017].
Sulaiha et al., "I am hot, irritable and feeling low; what alternatives do I have besides hormone replacement therapy?" Malaysian Family Physician, 50(3), Jan. 1, 2010, 1985-2274.
Anonymous: "Softgel capsule Vitamin E 100, 200, 400, 600 IU", Feb. 3, 2017, retrieved from the Internet URL:http://www.zahravi.com/en/Product/item/Products/Softgel Capsule/53/E-Zavit [retrieved on Feb. 13, 2017].
Soelaiman, et al.: "Palm Tocotrienol Supplementation Enhanced Bone Formation in Oestrogen-Deficient Rats", International J of Endocrinology, vol. 2012, Jan. 1, 2012 (Jan. 1, 2012), pp. 1-7, XP055372228,US ISSN: 1687-8337, DOI: 10.1155/2012/532862.
Rasool et al., Dose Dependent Elevation of Plasma Tocotrienol Levels and Its Effect on Arterial 12 Compliance, Plasma Total Antioxidant Status, and Lipid Profile in Healthy Humans Supplemented with Tocotrienol Rich Vitamin E, Journal of Nutritional Science and Vitaminology, vol. 52, No. 6 p. 473-478 (2006) abstract, p. 475-477, Fig 1, legend.
NutraSource, Generally Recognized as Safe (GRAS) Determination for the Use of Palm 16, 18 Tocotrienol Rich Fractions (TRF) as Ingredients in Food, GRAS Notice (GRN) No. 307, pp. 1-257 (Oct. 200~); available at, http://www.fda.gov/Food/FoodIngredientsPackaging/GenerallyRecognizedasSafeGRAS/GRASListings/default.htm; accessed on Jan. 5, 2015 (Jan. 5, 2015) p. 13-21, Tables 2-1 to 2-31.
Office Action issued in Chinese Application No. 201480046613.7, dated Feb. 13, 2017.

(Continued)

*Primary Examiner* — Jeffrey S Lundgren
*Assistant Examiner* — Tori Strong
(74) *Attorney, Agent, or Firm* — Meunier Carlin & Curfman LLC

(57) ABSTRACT

The present invention provides methods to reduce the number and severity of hot flashes utilizing tocotrienols. In particular, symptoms of perimenopause and menopause may be treated using the present methods. The present invention also provides methods to increase tissue concentrations of tocotrienols.

8 Claims, 5 Drawing Sheets

(56) References Cited

OTHER PUBLICATIONS

International Search Report and Written Opinion issued in International Application No. PCT/US2014/047633, dated Jan. 22, 2015.
European Search Report and Opinion issued in European Application No. 14829423.4, dated May 22, 2017.
Supplementary Search Report issued in European Application No. 14829423.4, dated Feb. 21, 2017.

* cited by examiner

METHODS FOR REDUCING THE OCCURRENCE OF HOT FLASHES

CROSS REFERENCE TO RELATED APPLICATIONS

This application claims the benefit PCT/US2014/047633 filed Jul. 22, 2014 which claims the benefit of U.S. Provisional Application No. 61/857,087 filed Jul. 22, 2013, the entire disclosure of which is expressly incorporated herein by reference for all purposes.

STATEMENT REGARDING FEDERALLY SPONSORED RESEARCH

This invention was made with U.S. government support under grant TL1RR025753 and NS42617 from the National Institutes of Health. The government has certain rights in this invention.

BACKGROUND OF THE INVENTION

The natural vitamin E family is composed of eight members, equally divided into two classes; tocopherols (TCP) and tocotrienols (TE). TCP are characterized by a saturated phytyl side chain with three chiral carbons whereas TE possess a farnesyl side chain with double bonds at carbons 3, 7, and 11. Within each class, isomers are differentiated by α, β, γ, and δ according to the position and degree of methylation on the chromanol head. TCP represent the primary form of vitamin E in green leafy vegetables, while TE are found in highest concentration in seeds of monocotyledons that include the wheat, rice, oat, barley, and palm.

Clinical trials testing the effects of vitamin E in a wide range of major health disorders have come to the general conclusion that vitamin E either is not helpful or could be harmful under certain conditions. Meta-analyses of over 20 randomized, controlled clinical trials testing vitamin E have now reached conclusions that on one hand serve the basis for readjusting public policies and practices while on the other suffer from a major blind spot which is not recognized in any of these reports. While title claims of such meta-analyses address vitamin E as whole, they fail to recognize that the form of vitamin E studied in the vast majority of these trials is α-tocopherol which represents one-eighth of the natural vitamin E family.

Vitamin E is a fat-soluble vitamin that exists in eight different forms. Each form has its own biological activity, which is the measure of potency or functional use in the body. Vitamin E is a dietary antioxidant that assists in maintaining cell integrity. It is obtained from sunflower, safflower, canola, and olive oils; also from many grains, nuts, fruits as well as fatty parts of meats. The tocotrienol form of natural vitamin E is found in rice and cereals but more abundantly in palm oil. Palm oil is an integral part of daily diet in southeastern Asia.

Palm oil represents a major source of natural tocotrienol. Tocotrienol compounds possess powerful neuroprotective, antioxidant, anti-cancer and cholesterol lowering properties that often differ from the properties of tocopherol. Micromolar amounts of tocotrienol suppress the activity of HMG-CoA reductase, the hepatic enzyme responsible for cholesterol synthesis. The unsaturated side chain of tocotrienol allows for more efficient penetration into tissues that have saturated fatty layers such as the brain and liver. Comparative examination of the antioxidant properties of tocopherol and tocotrienol revealed that tocotrienol is advantageous because of a better distribution in the fatty layers of the cell membrane. Like tocopherol, tocotrienols have been identified to possess distinct functions that may benefit human health, yet tocotrienol accounts for a very small fraction of overall vitamin E research.

Hot flashes, also referred to as vasomotor symptoms (VMS), typically begin as a sudden sensation of heat centered on the face and upper chest that rapidly becomes generalized. The sensation of heat lasts between two and four minutes, is often associated with profuse perspiration and occasionally palpitations, and is often followed by chills and shivering. Hot flashes cause arousal from sleep, leading to sleep disturbances.

Hot flashes occur in 75% of menopausal women in the United States. The flashes most often begin in the perimenopausal period, although in some women they do not begin until after menopause. Hot flashes usually occur several times per day, although the range may be from only one or two each day to as many as one per hour during the day and night. More than 80% of women who have hot flashes will continue to have them for more than one year. Untreated, hot flashes stop spontaneously within a few years of onset in most women. However, some women have hot flashes that persist for many years.

Hot flashes occur in about 70-80% of men undergoing androgen deprivation therapy in the treatment of prostate cancer. Men who develop hot flashes during temporary androgen deprivation usually recover within a few months of stopping treatment, however men receiving permanent androgen deprivation therapy may have persistent recurring hot flashes.

Hot flashes have been treated with hormone therapy, antidepressants, anti-seizure medications, and palliative care. However, many of these treatments may be contraindicated for some patients. There is an unmet need for further treatment options that are safe and effective.

SUMMARY OF THE INVENTION

Disclosed herein are methods to reduce the number of hot flashes in a subject with hot flashes, comprising: a) administering to a subject with hot flashes at least one tocotrienol selected from the group consisting of: alpha-tocotrienol; beta-tocotrienol; gamma-tocotrienol; and delta-tocotrienol; and b.) reducing the number of hot flashes in the subject.

Also provided are methods to reduce the severity of hot flashes in a subject with hot flashes, comprising: a.) administering to a subject with hot flashes at least one tocotrienol selected from the group consisting of: alpha-tocotrienol; beta-tocotrienol; gamma-tocotrienol; and delta-tocotrienol to a subject with hot flashes; and b.) reducing the severity of hot flashes in the subject.

Also provided are methods to eliminate hot flashes in a subject with hot flashes, comprising: a) administering to a subject with hot flashes at least one tocotrienol selected from the group consisting of: alpha-tocotrienol; beta-tocotrienol; gamma-tocotrienol; and delta-tocotrienol to a subject with hot flashes; and b) eliminating hot flashes in the subject.

Also provided are methods to ameliorate the symptoms of perimenopause in a subject, comprising: a) administering to a subject with symptoms of perimenopause at least one tocotrienol selected from the group consisting of: alpha-tocotrienol; beta-tocotrienol; gamma-tocotrienol; and delta-tocotrienol; and b.) ameliorating the symptoms of perimenopause in the subject.

Also provided are methods to ameliorate the symptoms of menopause in a subject, comprising: a) administering to a subject with symptoms of menopause at least one tocotrienol selected from the group consisting of: alpha-tocotrienol; beta-tocotrienol; gamma-tocotrienol; and delta-tocotrienol; and b.) ameliorating the symptoms of menopause in the subject.

Also provided are methods herein, wherein the tocotrienol is administered according to Table A.

Also provided are methods herein, wherein the tocotrienol is administered according to Table B.

Also provided are methods herein, wherein the tocotrienol is administered according to Table C.

Also provided are methods herein, wherein the tocotrienol is administered according to Table D.

Also provided are methods herein, wherein the tocotrienol is administered according to Table E.

Also provided are methods herein, which further comprises administering an additional pharmaceutical composition.

Also provided are methods herein, which further comprises administering a composition selected from the group consisting of: progesterone; and estrogen.

Also provided are methods herein, wherein the tocotrienol administered comprises tocopherol, by weight percent of total, less than a percent selected from the group consisting of: 50%; 40%; 30%; 20%; 15%; 10%; 5%; and 1%.

Also provided are methods herein, wherein the tocotrienol is substantially free of tocopherol.

Also provided are methods herein, wherein tissue concentration of at least one tocotrienol in the subject after administration is selected from the group consisting of about: at least about 0.5 μm/L to at least about 50 μm/L; at least about 1 μm/L to at least about 40 μm/L; at least about 2 μm/L to at least about 30 μm/L; at least about 3 μm/L to at least about 25 μm/L; at least about 4 μm/L to at least about 20 μm/L; and at least about 5 μm/L to at least about 15 μm/L.

Also provided are methods herein, wherein the tocotrienol is derived from at least one plant selected from the group consisting of: wheat; rice; barley; and palm.

Also provided are methods herein, wherein the tocotrienol is derived from palm oil.

Also provided are methods herein, wherein the tocotrienol is 400 mg to 800 mg per day of Tocovid SupraBio.

Also provided are methods to reduce the number of hot flashes in a subject with hotflashes, comprising: a) administering at least one daily 400 mg to 800 mg dose of tocotrienol formulation to a subject with hot flashes, wherein the tocotrienol formulation comprises approximately 123 mg to approximately 146 mg d-alpha tocotrienol; approximately 16 mg to approximately 32 mg d-beta tocotrienol; approximately 225 mg to approximately 450 mg d-gamma tocotrienol; and approximately 51 mg to approximately 102 mg d-delta tocotrienol; and b.) reducing the number of hot flashes in the subject.

Also provided are reduce the severity of hot flashes in a subject with hot flashes, comprising: a) administering at least one daily 400 mg to 800 mg dose of tocotrienol formulation to a subject with hot flashes, wherein the tocotrienol formulation comprises approximately 123 mg to approximately 146 mg d-alpha tocotrienol; approximately 16 mg to approximately 32 mg d-beta tocotrienol; approximately 225 mg to approximately 450 mg d-gamma tocotrienol; and approximately 51 mg to approximately 102 mg d-delta tocotrienol; and b.) reducing the severity of hot flashes in the subject.

Also provided are eliminate hot flashes in a subject with hot flashes, comprising: a.) administering at least one daily 400 mg to 800 mg dose of tocotrienol formulation to a subject with hot flashes, wherein the tocotrienol formulation comprises approximately 123 mg to approximately 146 mg d-alpha tocotrienol; approximately 16 mg to approximately 32 mg d-beta tocotrienol; approximately 225 mg to approximately 450 mg d-gamma tocotrienol; and approximately 51 mg to approximately 102 mg d-delta tocotrienol; and b.) eliminating hot flashes in the subject.

Also provided are methods to ameliorate the symptoms of perimenopause in a subject, comprising: a) administering at least one daily 400 mg to 800 mg dose of tocotrienol formulation to a subject with hot flashes, wherein the tocotrienol formulation comprises approximately 123 mg to approximately 146 mg d-alpha tocotrienol; approximately 16 mg to approximately 32 mg d-beta tocotrienol; approximately 225 mg to approximately 450 mg d-gamma tocotrienol; and approximately 51 mg to approximately 102 mg d-delta tocotrienol; and b.) ameliorating the symptoms of perimenopause in the subject.

Also provided are methods to ameliorate the symptoms of menopause in a subject, comprising: a) administering at least one daily 400 mg to 800 mg dose of tocotrienol formulation to a subject with hot flashes, wherein the tocotrienol formulation comprises approximately 123 mg to approximately 146 mg d-alpha tocotrienol; approximately 16 mg to approximately 32 mg d-beta tocotrienol; approximately 225 mg to approximately 450 mg d-gamma tocotrienol; and approximately 51 mg to approximately 102 mg d-delta tocotrienol; and b.) ameliorating the symptoms of menopause in the subject.

BRIEF DESCRIPTION OF THE FIGURES

FIG. 3A: δ-TE. FIG. 3B: γ-TE. FIG. 3C: γ-TCP.

FIG. 4A: δ-TE. FIG. 4B: γ-TE. FIG. 4C: γ-TCP.

DETAILED DESCRIPTION OF THE INVENTION

Figure 1A:
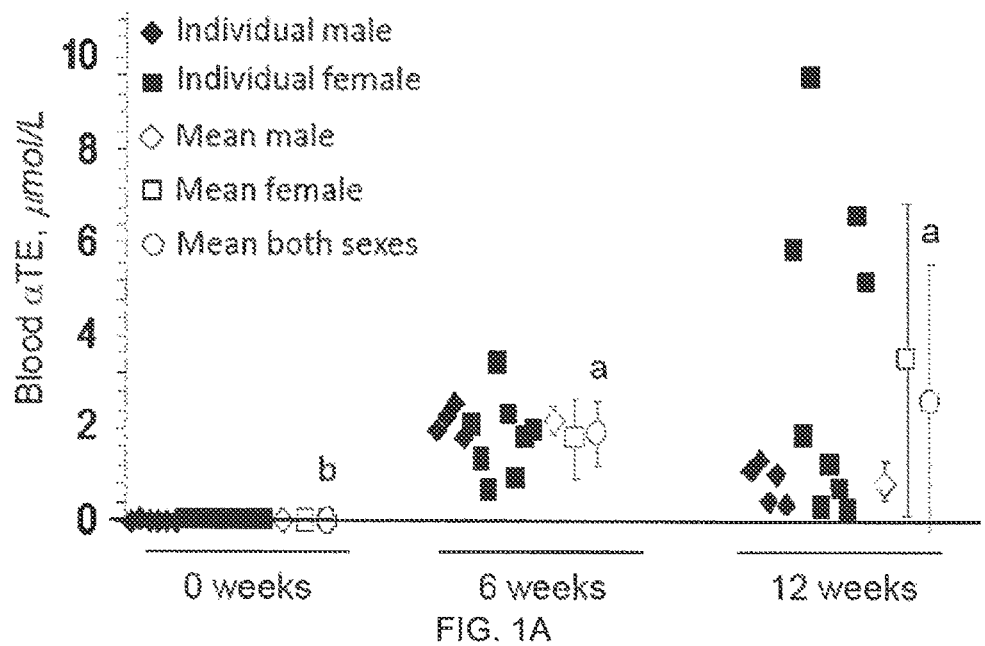
FIGS. 1A-1B: Human whole blood alpha tocotrienol (αTE) (FIG. 1A) and alpha tocopherol (αTCP) (FIG. 1B) concentration following oral TE supplementation. Data represent individual values (males n=6, females n=10) and mean±SD at baseline (0 week), 6 weeks and 12 weeks. Within each treatment group, levels without a common letter differ, P<0.05.

Subjects in a trial for oral TE supplementation reported reduced number and severity of hot flashes.

Tissue and Organ Availability of TE.

The present invention discloses the tissue availability of TE in vital organs of adult humans following oral supplementation, and characterizes multiple vital organ concentration of TCP in adults. Patients supplemented for even the shortest duration had detectable levels of TE in tissue. That TE was delivered and accumulated in vital human organs demonstrates that oral TE supplementation enriches its concentration in whole blood, adipose, skin, brain, cardiac muscle, and liver.

TABLE A

Tocotrienol daily dose, by milligrams:

| Tocotrienol | Range 1 | Range 2 | Range 3 | Range 4 |
|---|---|---|---|---|
| alpha | 100-150 | 110-140 | 115-130 | 120-125 |
| gamma | 180-270 | 190-260 | 200-250 | 220-230 |
| delta | 35-70 | 40-65 | 45-60 | 48-54 |

TABLE B

Tocotrienol w/w percent, by total tocotrienols:

| Tocotrienol | Range 1 | Range 2 | Range 3 | Range 4 |
|---|---|---|---|---|
| alpha | 0-50 | 20-40 | 25-35 | 28-32 |
| gamma | 0-70 | 45-65 | 50-60 | 54-58 |
| delta | 0-25 | 5-20 | 8-15 | 10-14 |

TABLE C

Tocotrienol, by doses per day:

| Tocotrienol | Range 1 | Range 2 | Range 3 | Range 4 |
|---|---|---|---|---|
| alpha | 0-6 | 1-5 | 2-4 | 1-2 |
| gamma | 0-6 | 1-5 | 2-4 | 1-2 |
| delta | 0-6 | 1-5 | 2-4 | 1-2 |

TABLE D

Tocotrienol doses, by number of days per week:

| Tocotrienol | Range 1 | Range 2 | Range 3 | Range 4 |
|---|---|---|---|---|
| alpha | 0-7 | 1-6 | 2-5 | 6-7 |
| gamma | 0-7 | 1-6 | 2-5 | 6-7 |
| delta | 0-7 | 1-6 | 2-5 | 6-7 |

TABLE E

Tocotrienol doses, by number of weeks per year:

| Tocotrienol | Range 1 | Range 2 | Range 3 | Range 4 |
|---|---|---|---|---|
| alpha | .5-52 | 1-20 | 4-20 | 4-12 |
| gamma | .5-52 | 1-20 | 4-20 | 4-12 |
| delta | .5-52 | 1-20 | 4-20 | 4-12 |

EXAMPLES

Example 1. Experimental Methods

Product and Dosage Used in this Study 200 mg gel-capsules containing tocotrienol or vehicle only (placebo) gel capsules were provided by Carotech Inc, New Jersey. TCT is sold over the counter for general human consumption in the United States and many other countries.

| TOCOTRIENOL GEL CAPSULE (200 mg) | |
|---|---|
| Ingredients | mg |
| Tocomin ® 50 | 200.0 |
| Soya Oil | 305.4 |
| Labrasol ® | 50.0 |
| Cremophor EL ® | 50.0 |

Ingredient Function

Tocomin® 50—

Contains a minimum of 50% vitamin E whereby approximately 10% is alpha-tocopherol, 12% of alpha-tocotrienols, 20.6% of gamma-tocotrienols, 1.5% of beta-tocotrienols and 5% of delta-tocotrienols. Tocomin® 50 is produced by Carotech Bhd, Malaysia and has been registered as a GRAS certified supplement by the FDA for oral supplementation.

Soya Oil—

Commonly known as soybean oil, soya oil is a widely used cooking oil in the United States. Soya oil is used by the food industry in a number of food products including salad dressings, sandwich spreads, margarine, bread, mayonnaise, non-dairy coffee creamers and snack foods. Soya oil is used as a carrier and bulking agent in the formulation.

Labrasol®—

Product from Gattefosse SAS, France. It is a mixture of caprylocaproyl polyoxyglycerides and caprylocaproyl macrogolglycerides. Functions as a liquid solubilizer to produce a self emulsifying system. It is monographed in USP/NF latest edition under the monograph's title caprylocaproyl polyoxyglycerides and in the European pharmacopeia under the monograph's title caprylocaproyl macrogolglycerides.

Cremophor EL®—

Product from BASF, Germany. Functions as an emulsifying agent and solubilizing agent. Its nonproprietary name is polyoxyl 35 castor oil as listed in USP/NF. It is widely used in oral, topical and parenteral pharmaceutical formulations as well as in cosmetics and animal feed. It is listed in the FDA inactive Ingredients Guide (IV injections and ophthalmic solutions) and also included in parenteral medicines licensed in UK (Handbook of Pharmaceutical Excipients, 4th Edition, 2003, published by the Pharmaceutical Press and the American Pharmaceutical Association).

| PLACEBO GEL CAPSULE (200 mg) | |
|---|---|
| Ingredients | mg |
| Soya Oil | 505.4 |
| Labrasol ® | 50.0 |
| Cremophor EL ® | 50.0 |

NOTE:
The balance of gel capsule content by removing Tocomin 50 is made up by Soya Oil.

Example 2. Phase I Trial—Healthy Subject

Design

Randomized, double-blinded, placebo-controlled, single center clinical trial.

60 Healthy participants, MAD test groups (n=10):
Placebo (PBO)–vehicle control
PBO+low dose aspirin (81 mg)
200 mg oral TCT twice per day (400 mg total per day)
200 mg oral TCT four times per day (800 mg total per day)

200 mg oral TCT twice per day (400 mg total per day)+low dose aspirin (81 mg)

200 mg oral TCT four times per day (800 mg total per day)+low dose aspirin (81 mg)

Oral supplementation with clinical evaluation at baseline, 3 mos, and 6 mos following supplementation.

Inclusion Criteria:

Healthy subjects between 40 and 70 years of age

No history of long-term vitamin E supplement (defined as daily oral tocopherol or tocotrienol supplementation 6 mos; within the past 5 years)

No current vitamin E supplementation in multi-vitamin

Monitor blood parameters every month for 6 mos:

Platelet function testing—aggregation and activation tests will be performed as described CBC—complete blood count Lipid profile (total cholesterol, high density lipoprotein cholesterol, low density lipoprotein cholesterol, triglycerides)

Blood pressure

Hepatic function panel (total protein, albumin, bilirubin, alkaline phosphatase, alanine aminotransferase, aspartate aminotransferase)

HPLC vitamin E analysis of tape strips is performed to assess compliance. Tape stripping is a minimally invasive procedure used to assess compliance following oral TCT supplementation. It involves sequential removal of 0.5-1 µl layers of the skin by sticking and removing an adhesive disc. Tape stripping does not break the skin and causes only mild irritation similar to sticking and removing scotch tape to skin. Tape stripping does not compromise skin barrier function. The procedure conforms with US Food & Drug Administration published guidance for tape stripping 199849. In brief, the tape stripping procedure consists of taking two sequential tape strips from one medial fore-arm (which are discarded) followed by ten sequential strippings from the same location which are used for evaluation. The skin area stripped is cleaned with ethanol before the procedure is performed.

Study Procedure.

Treatment Chronology

Healthy consenting subjects are enrolled and selected according to study parameters.

Initial Visit:

At the initial appointment with the research nurse, the subject signs the consent and HIPAA forms. The Research Nurse records the subject's blood pressure and takes a baseline blood draw (20 ml) for platelet function, complete blood count, lipid profile, hepatic function panel and vitamin E content. Baseline tape-stripping is performed. Participants are at that time be given a 1-month supply of supplements (PBO or TCT alone or with low-dose aspirin). A baseline health questionnaire is conducted.

1-Month Visit:

Subjects are asked to return with the prior month's pill packs for compliance counting. The Research Nurse performs blood pressure measurement and tape stripping after which subjects are given their next month's supply of pills. A brief health questionnaire is conducted.

2-Month Visit:

Subjects are asked to return with the prior month's pill packs for compliance counting. The Research Nurse performs blood pressure measurement and tape stripping after which subjects are given their next month's supply of pills. A brief health questionnaire is conducted.

3-Month Visit:

The Research Nurse records the subject's blood pressure and takes a blood draw (20 ml) for testing platelet function, complete blood count, lipid profile, hepatic function panel, and vitamin E content. Subjects are asked to return with the prior month's pill packs for compliance counting. The Research Nurse performs tape stripping after which subjects are given their next month's supply of pills. A brief health questionnaire is conducted.

4-Month Visit:

Subjects are asked to return with the prior month's pill packs for compliance counting. The Research Nurse performs blood pressure measurement and tape stripping after which subjects are given their next month's supply of pills. A brief health questionnaire is conducted.

5-Month Visit:

Subjects are asked to return with the prior month's pill packs for compliance counting. The Research Nurse performs blood pressure measurement and tape stripping after which subjects are given their next month's supply of pills. A brief health questionnaire is conducted.

6-Month Visit:

The Research Nurse records the subject's blood pressure and takes a blood draw (20 ml) for testing platelet function, complete blood count, lipid profile, hepatic function panel, and vitamin E content. Subjects are asked to return with the prior month's pill packs for compliance counting. The Research Nurse performs tape stripping. A final health questionnaire is conducted.

Adverse Events:

There have been no related adverse affects in the previously tested IRB protocols in which patients received TCT supplementation for >1 yr. In this protocol, patients are supplemented with 400 mg or 800 mg TCT for 6 mos.

Subjects answer a health questionnaire each month during their site visit. The Research Nurse asks questions related to myalgia, bleeding complication, and skin discoloration (ie. jaundice as sign of liver problem).

Example 3. Case Study Subject #1

A healthy volunteer 52 year old perimenopausal or menopausal woman with hot flashes supplemented her diet with 800 mg Tocovid Suprabio per day, for three months. Administrators of the supplementation trial did not ask any of the subjects about hot flash symptoms. However, during a monthly meeting after beginning the regimen, this woman volunteered that she stopped having hot flashes while supplementing her diet with 800 mg daily Tocovid Suprabio. Moreover, at a follow-up visit after a one month "wash-out" time period (no supplementation), this same woman volunteered that she had resumed having hot flashes.

Example 4. Case Study Subject #2

A healthy volunteer 51 year old perimenopausal or menopausal woman with hot flashes supplemented her diet with 800 mg mg Tocovid Suprabio per day, for three months. The woman stopped having hot flashes while supplementing her diet with 800 mg daily Tocovid Suprabio.

Example 5. Case Study Subject #3

A healthy volunteer 49 year old perimenopausal or menopausal woman with hot flashes supplemented her diet with 800 mg mg Tocovid Suprabio per day, for three months. The woman stopped having hot flashes while supplementing her diet with 800 mg daily Tocovid Suprabio.

Example 6. Case Study Subject #4

A healthy volunteer perimenopausal or menopausal woman with hot flashes supplemented her diet with 400 mg mg Tocovid Suprabio per day, for three months. The woman stopped having hot flashes while supplementing her diet with 400 mg daily Tocovid Suprabio.

Example 7. Tissue Effects of Supplementation

Figure 1B:
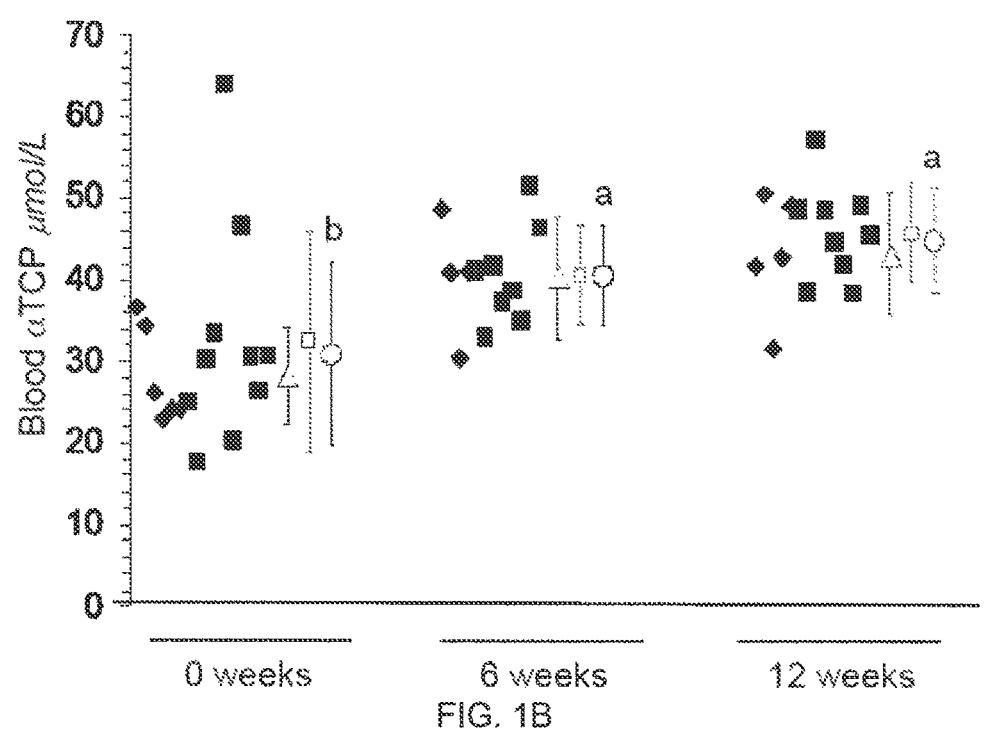
Figure 2A:
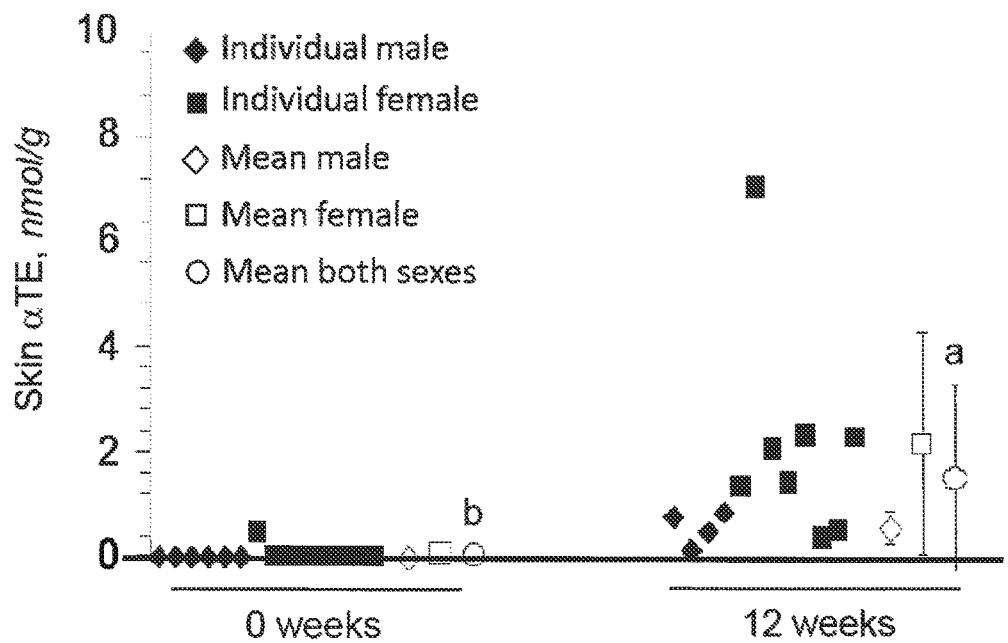
FIGS. 2A-2B: Human skin αTE (FIG. 2A) and αTCP (FIG. 2B) concentration following oral TE supplementation. Data represent individual values (males n=6, females n=10) and mean±SD at baseline (0 wk) and 12 wk. Within each treatment group, levels without a common letter differ, P<0.05.
Figure 2B:
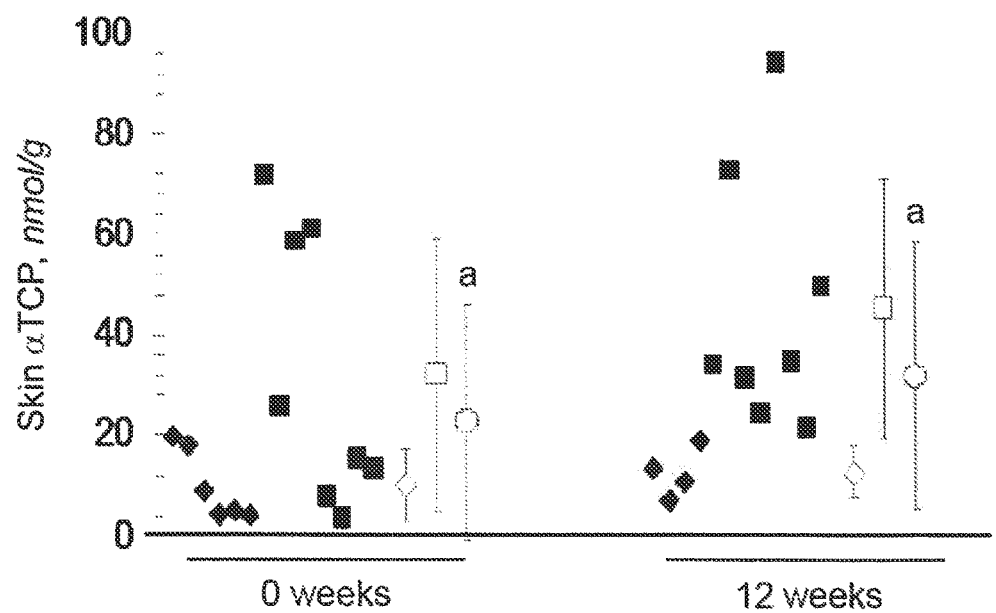
Figure 3A:
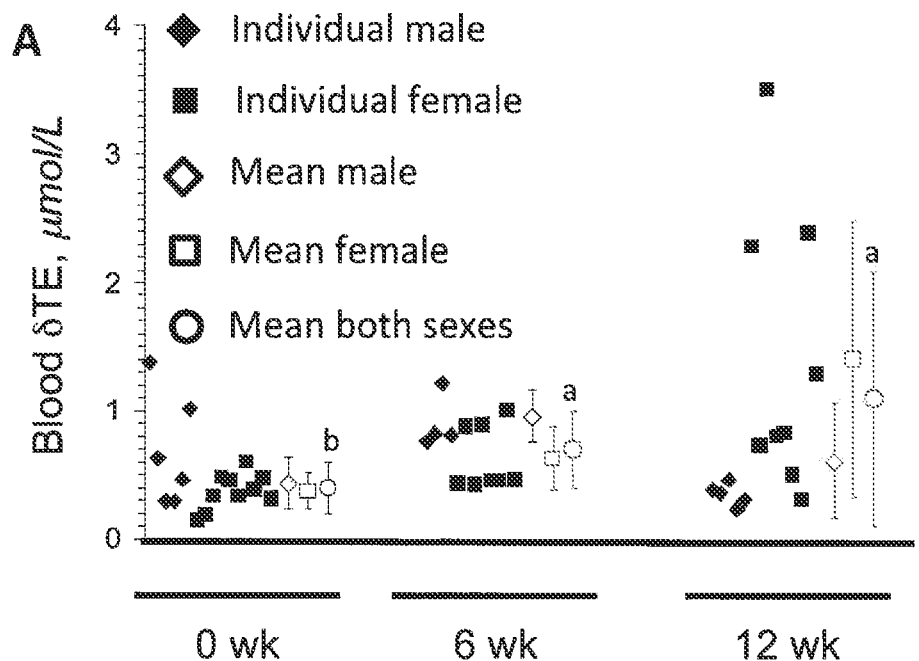
FIGS. 3A-3C: Human blood TE and TCP concentration following oral TE supplementation at baseline (0 wk), 6 wk and 12 wk.
Figure 3B:
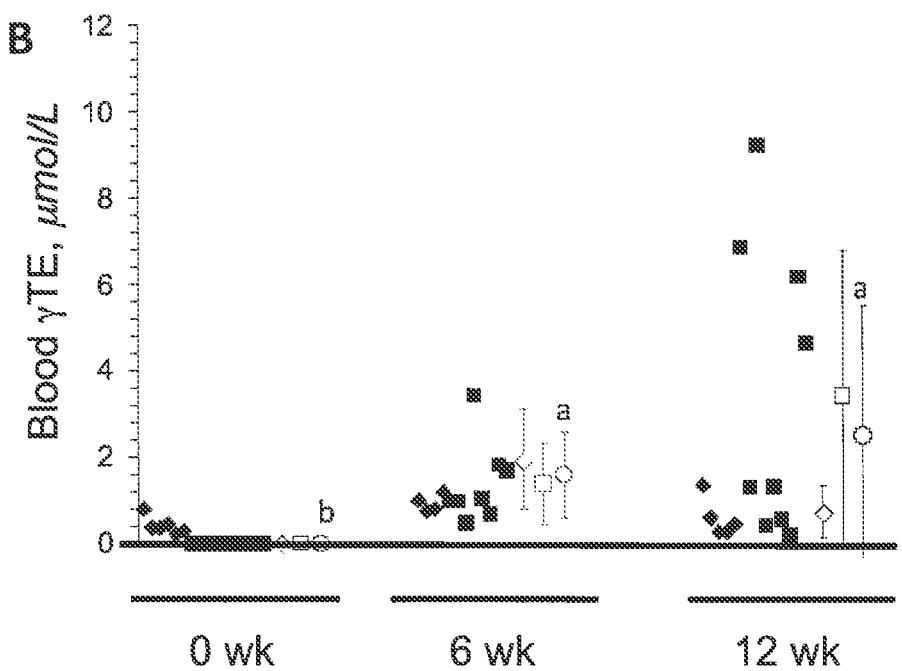
Figure 3C:
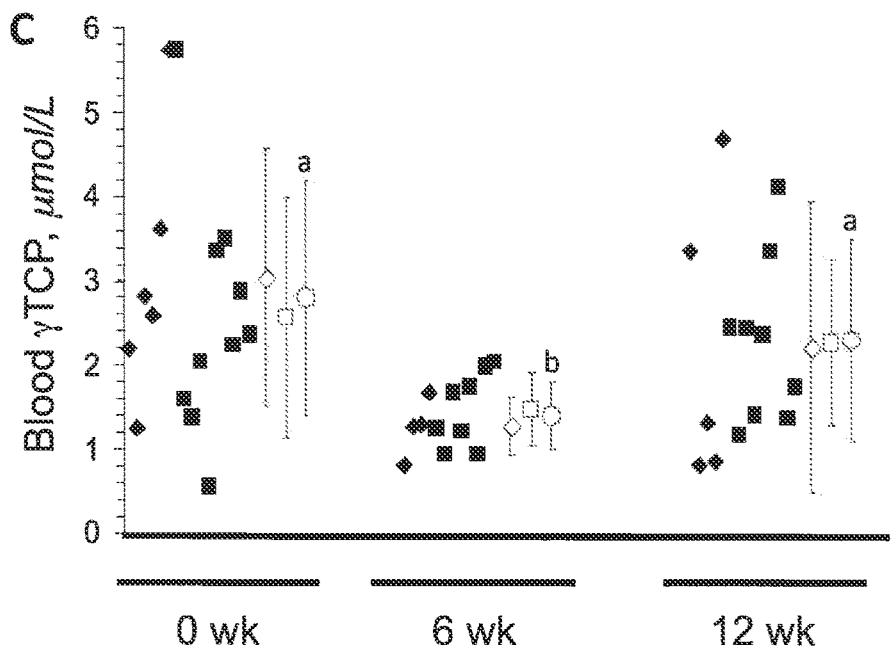
Figure 4A:
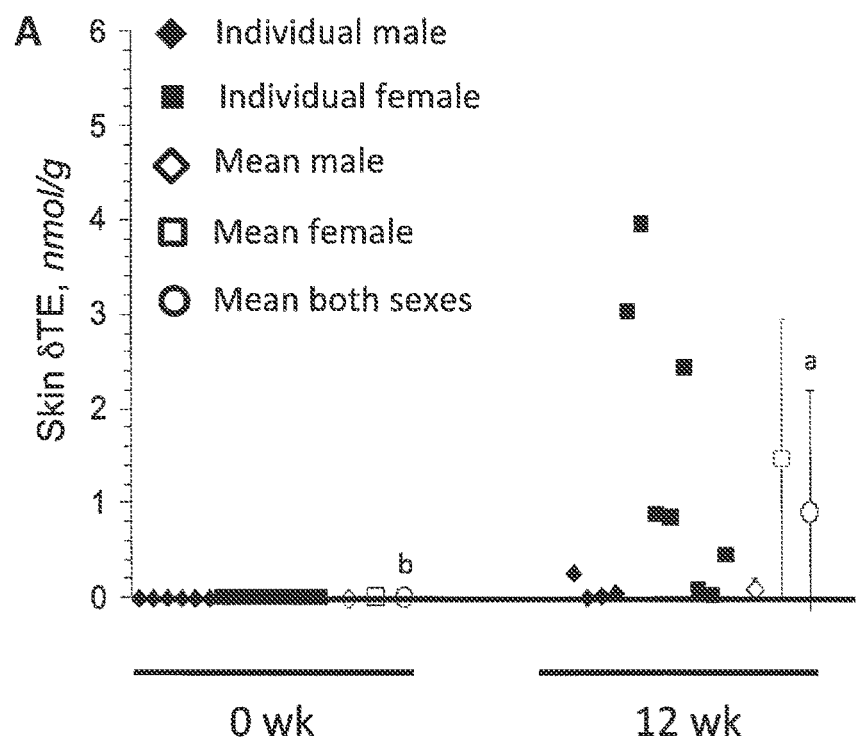
FIGS. 4A-4C: Human skin TE and TCP concentration following oral TE supplementation at baseline (0 wk) and 12 wk.
Figure 4B:
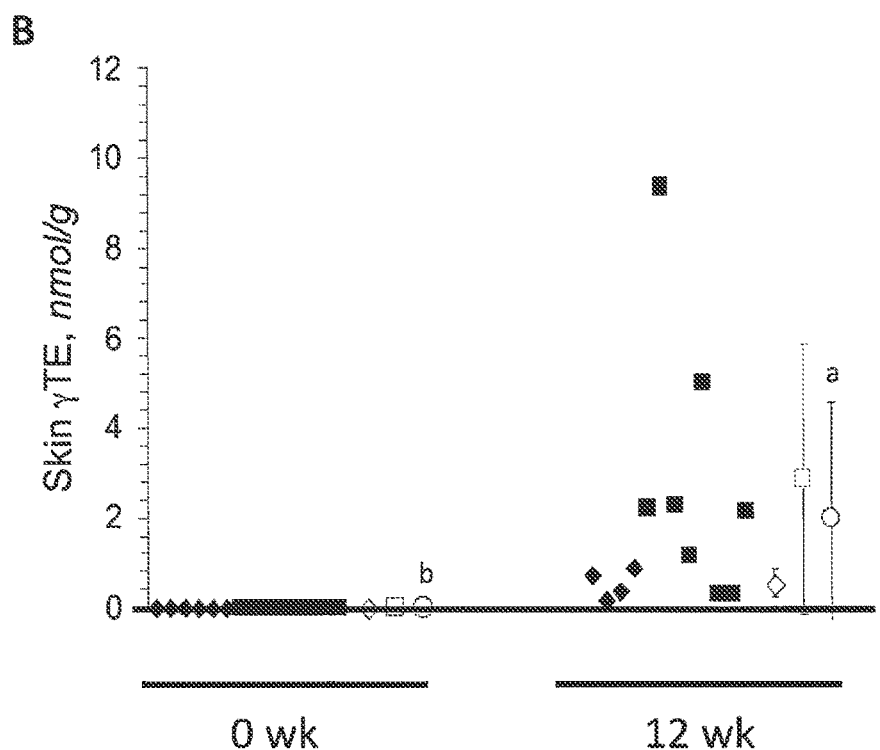
Figure 4C:
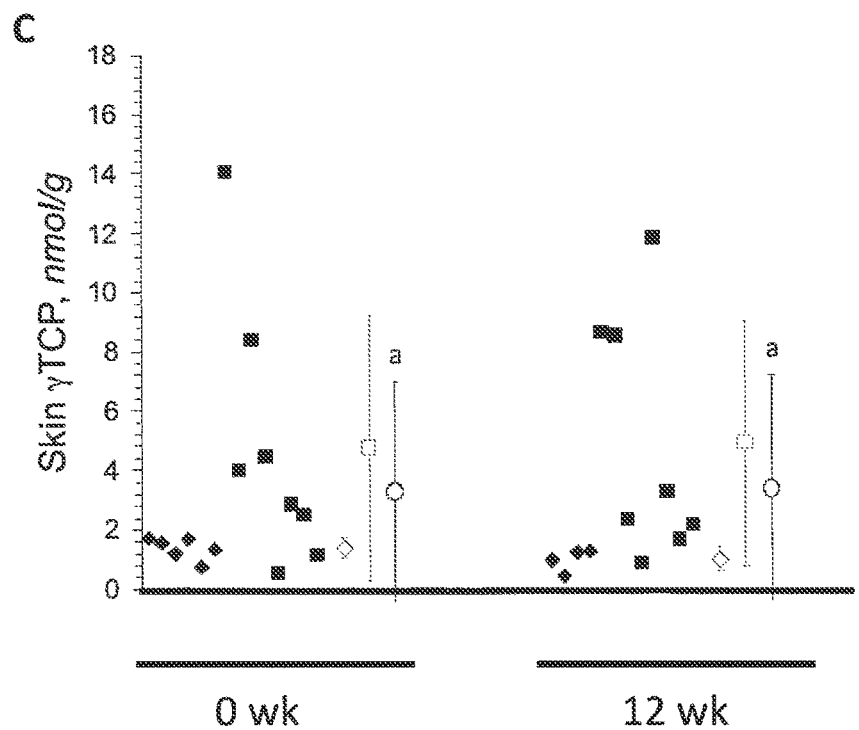

Now turning to FIGS. 1-4, effects of supplementation are shown. Baseline levels of TE, as opposed to TCE, are very low. Measurements of TE show baseline levels at less than 1 micromole per liter for blood and less than 1 nanomole per gram for skin. Daily TE supplementation, over the course of weeks, results in a marked increase in tissue concentrations of TE.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. Whenever a range is given in the specification, all intermediate ranges and sub-ranges, as well as all individual values included in the ranges given are intended to be included in the disclosure. When a Markush group or other grouping is used herein, all individual members of the group and all combinations and sub-combinations possible of the group are intended to be individually included in the disclosure.

In general the terms and phrases used herein have their art-recognized meaning, which can be found by reference to standard texts, journal references and contexts known to those skilled in the art. The above definitions are provided to clarify their specific use in the context of the invention.

What is claimed is:

1. A method to ameliorate one or more symptoms of perimenopause or menopause in a subject having perimenopause or menopause, or to ameliorate hot flashes in a subject receiving androgen deprivation therapy, comprising:
   a) administering to the subject having symptoms of perimenopause or menopause, or to the subject receiving androgen deprivation therapy, a tocotrienol formulation comprising at least 10% alpha-tocopherol, at least 12% alpha-tocotrienols, at least 20.6% gamma-tocotrienols, at least 1.5% beta-tocotrienols, and at least 5% delta-tocotrienols; and
   b) ameliorating the symptoms of perimenopause or menopause in the subject having perimenopause or menopause, or ameliorating hot flashes in the subject receiving androgen deprivation therapy.

2. The method of claim 1, which further comprises administering an additional pharmaceutical composition.

3. The method of claim 1, which further comprises administering a composition selected from the group consisting of: progesterone; and estrogen.

4. The method of claim 1, wherein the tocotrienol formulation administered comprises tocopherol, by weight percent of total, less than a percent selected from the group consisting of: 50%; 40%; 30%; 20%; and 15%.

5. The method of claim 1, wherein the administering step comprises administering at least one dose of the tocotrienol formulation to the subject receiving androgen deprivation therapy, wherein the subject has hot flashes, wherein the tocotrienol formulation comprises approximately 123 mg to approximately 146 mg d-alpha tocotrienol; approximately 16 mg to approximately 32 mg d-beta tocotrienol; approximately 225 mg to approximately 450 mg d-gamma tocotrienol; and approximately 51 mg to approximately 102 mg d-delta tocotrienol; and wherein the ameliorating step comprises reducing the severity of hot flashes in the subject receiving androgen deprivation therapy.

6. The method of claim 1, wherein the administering step comprises administering at least one dose of the tocotrienol formulation to the subject having perimenopause, wherein the tocotrienol formulation comprises approximately 123 mg to approximately 146 mg d-alpha tocotrienol; approximately 16 mg to approximately 32 mg d-beta tocotrienol; approximately 225 mg to approximately 450 mg d-gamma tocotrienol; and approximately 51 mg to approximately 102 mg d-delta tocotrienol; and wherein the ameliorating step comprises ameliorating one or more symptoms of perimenopause in the subject having perimenopause.

7. The method of claim 1, wherein the administering step comprises administering at least one dose of the tocotrienol formulation to the subject having menopause, wherein the tocotrienol formulation comprises approximately 123 mg to approximately 146 mg d-alpha tocotrienol; approximately 16 mg to approximately 32 mg d-beta tocotrienol; approximately 225 mg to approximately 450 mg d-gamma tocotrienol; and approximately 51 mg to approximately 102 mg d-delta tocotrienol; and wherein the ameliorating step comprises ameliorating one or more symptoms of menopause in the subject having menopause.

8. The method of claim 1, wherein the administering step comprises administering an oral formulation comprising the tocotrienol formulation, wherein the tocotrienol formulation comprises a minimum of 50% vitamin E.

* * * * *